(12) United States Patent
Van Dulmen et al.

(10) Patent No.: US 6,469,306 B1
(45) Date of Patent: Oct. 22, 2002

(54) METHOD OF IMAGING BY SPECT (76) Inventors: Adrianus A. Van Dulmen, NL-1871, CZ Schoorl (NL); Stéphan Walrand, 31, rue de Baileux, B-5630 Silenrieux (BE)

(*) Notice: Subject to any disclaimer, the term of this patent is extended or adjusted under 35 U.S.C. 154(b) by 0 days.

(21) Appl. No.: 09/485,841
(22) PCT Filed: Jul. 30, 1998
(86) PCT No.: PCT/EP98/04994
§ 371 (c)(1),
(2), (4) Date: May 18, 2000
(87) PCT Pub. No.: WO99/09431
PCT Pub. Date: Feb. 25, 1999

(30) Foreign Application Priority Data

Aug. 19, 1997 (EP) .......................................... 97202538

(51) Int. Cl.$^7$ .............................................. G01T 1/166
(52) U.S. Cl. ............................... 250/363.04; 250/363.1
(58) Field of Search ........................ 250/363.1, 363.04

(56) References Cited

U.S. PATENT DOCUMENTS

| | | |
|---|---|---|
| 3,784,820 A | 1/1974 | Miraldi |
| 3,970,853 A | 7/1976 | Kuhl et al. |
| 4,774,410 A | 9/1988 | Hsieh |
| 4,849,638 A * | 7/1989 | Hawman ............... 250/363.02 |

FOREIGN PATENT DOCUMENTS

| | | |
|---|---|---|
| FR | 2 697 918 | 5/1994 |
| WO | WO 94 25879 | 11/1994 |

OTHER PUBLICATIONS

M.S. Rosenthal, J. Cullom, W. Hawkins, S.C. Moore, B.M.W. Tsui and Y. Yester, *The Journal of Nuclear Medicine*, vol. 36, No. 8, Aug., 1995 "Quantitative SPECT Imaging: A Review and Recommendations by the Focus Committee of the Society of Nuclear Medicine Computer and Instrumentation Council", pp 1489–1513.

Stephen C. Moore, Kypros Kouris, and Ian Cullum, *European Journal of Nuclear Medicine*, "Collimator design for single photon emission tomography", pp 138–150, 1992.

Dan J. Kadrmas, Ronald J. Jaszczak, James W. McCormick, R. Edward Coleman and Chun Bin Lim, *Phys. Med. Biol. 40 (1995)*, "Truncation artifact reduction in transmission CT for improved SPECT attenuation compensation", pp 1085–1104.

L. A. Shepp and Y. Vardi, *IEEE transactions on Medical Imaging*, vol. MI–I, No. 2, Oct., 1982 "Maximum Likelihood Reconstruction for Emission Tomography", pp 113–121.

Kenneth Lange and Richard Carson, *Journal of Computer Assisted Tomography*, vol. 8, No. 2, 1984, "EM Reconstruction Algorithms for Emission and Transmission Tomography", pp 306–316.

S. H. Manglos, *Phys Med. Biol. 1992*, vol. 37, No. 3, "Truncation artifact suppression in cone–beam radionuclide transmission CT using maximum likelihood techniques: evaluation with human subject", pp 549–561.

* cited by examiner

*Primary Examiner*—Constantine Hannaher
(74) *Attorney, Agent, or Firm*—Finnegan, Henderson, Farabow, Garrett, & Dunner, L.L.P.

(57) ABSTRACT

A method of imaging a target organ in a patient by SPECT, by using a gamma camera having a gamma detector provided with a fan-beam collimator (2), focusing to a focal line parallel to the patient's body length, and by computer reconstructing the distribution of the radioactivity inside the patient's body from the acquired planar images by using certain reconstruction algorithms. The images are acquired along at least one linear orbit performed in a direction perpendicular to the patient's body, and the collimator focal line is made to travel throughout said target organ during the acquisition. The invention further relates to an equipment for performing this method.

21 Claims, 3 Drawing Sheets fig. 1 fig. 2 fig. 3 fig. 4A fig. 4B
(Prior Art)

METHOD OF IMAGING BY SPECT

METHODS OF IMAGING BY SPECT

The invention relates to a method of imaging a target organ in a patient by SPECT, by using a 'gamma camera having a gamma detector provided with a fan-beam collimator, focusing to a focal line parallel to the patient's body length, and by computer reconstructing the distribution of the radioactivity inside the patient's body from the acquired planar images by using certain reconstruction algorithms.

The Single Photo Emission Computed Tomography (SPECT) is routinely used in clinical studies. SPECT is performed by using a gamma camera, comprising a collimator fixed on a gamma detector, which gamma camera follows a revolution orbit around the patient's body. The gamma rays, emitted by a radioactive tracer, accumulated in certain tissues or organs of the patient's body, are sorted by the collimator and recorded by the gamma detector under various angles around the body, the collimator always pointing to (facing) the rotation axis, of the camera. From the acquired planar images the distribution of the activity inside the patient's body can be computed using certain reconstruction algorithms. Generally the so-called Expectation-Maximization of the Maximum-Likelihood (EM-ML) algorithm is used, as described by Shepp et al. (IEEE Trans. Med. Imaging 1982; 2:113–122) and by Lange et al. (J. Comput. Assist. Tomogr. 1984; 8:306–316). This iterative algorithm minimizes the effect of noise in SPECT images.

The collimators nowadays is use are manufactured from a lead sheat perforated with a plurality of usually parallel holes. The collimator is the most problematic element of the SPECT device, with regard to its poor sensitivity (less than 0.01% of the gamma radiation passes the collimator and reaches the detector) and its poor spatial resolution, becoming increasingly worse with increasing distance between activity source (i.e. the organ or tissue wherein the radioactivity has been accumulated) and collimator. Improvement of one of these properties, e.g. by modifying the hole length or diameter of the collimator, is always to the detriment of the other one. Furthermore, the SPECT technique is inadequate in producing reliable images because of the fact that small fluctuations in the acquired data can involve significant variations in the reconstructed images. This is due to the geometry of the acquired data. The limited time available for obtaining the necessary information (because of the restricted fixation time of the patient and the decay time of the radioactive tracer) and the limited injected radioactivity dose (limited for health care reasons) lead to acquired images containing statistical noise. Indeed the measurement of a radioactive process follows the Poisson law, giving a signal to noise ratio proportional to the square root of the count rate. As a result, the reconstructed images are frequently corrupted by significant false positive information, so-called noise artefacts. Consequently, it is a major goal in SPECT imaging to increase the SPECT sensitivity without reduction of the spatial resolution in order to improve the acquired signal to noise ratio.

In an attempt to improve the sensitivity-resolution couple of the collimator, fan-beam collimators, focusing to a focal line, have been developed recently: see e.g. the review articles by Moore et al. (Eur. J. Nucl. Med. 1992; 19:138–150) and by Rosenthal et al. (J. Nucl. Med. 1995; 36:1489–1513). These collimators, having holes converging in one dimension to a focal line, have an increasingly better sensitivity-resolution couple when the activity source approaches the collimator focal line. By using a fan-beam collimator in the SPECT imaging technique, acquiring the images along the classical revolution orbit, the focal line is parallel to the axis of rotation of the gamma camera on the other side of the patient and consequently parallel to the patient's body length (see the above publication by Rosenthal et al., p. 1495). Nevertheless, the activity source, i.e. the target organ, has only a restricted approaching range with regard to the collimator focal line, because said organ and all activity contained in the same transverse (i.e. perpendicular to the patient's length) slice must be kept within the collimator acceptance angle during the acquisition by the rotating camera. Otherwise, the reconstructed images are corrupted by significant truncature artefacts. This problem of image truncation by using fan-beam collimators is discussed in more detail by Manglos et al. (Phys. Med. Biol. 1993; 38:1443–1457) and by Kadrmas et al. (Phys. Me.Biol. 1995; 40:1085–1101). The above requirement, viz. to keep all source activity, i.e. in fact the complete body diameter of the patient, within the collimator acceptance angle during the acquisition along a revolution orbit, limits the choice of fan-beam collimators to those having a relatively large focal length, viz. greater than approx. 60 cm, giving results not very different from those obtained with a parallel collimator. Therefore, the target organ cannot be positioned close to the focal line of the collimator where its sensitivity and spatial resolution are optimal. As a consequence, the sensitivity improvement, obtained by this technique for similar resolution, is limited to a factor of approx. 1.5 at most. Also the target of interest must be smaller than the detector transverse slice (preferably approx. 1.4 times smaller).

It is the objective of the present invention to provide a method of imaging by SPECT with a substantially improved sensitivity-resolution couple. In other words, it is the aim of the present invention to provide a method of SPECT imaging which results in substantially improved reconstructed images.

This objective can be achieved by a method as defined in the opening paragraph, viz. a method of SPECT imaging a target organ in a patient, by using a gamma camera having a gamma detector provided with a fan-beam collimator, focusing to a focal line parallel to the patient's body, followed by computer reconstruction of the radioactivity distribution from the acquired images, which method according to the present invention is characterized in that the images are acquired along at least on linear orbit performed in a direction perpendicular to the patient's body length, and in that the collimator focal line is made to travel throughout said target organ during the acquisition.

It has surprisingly been found, that by applying the above method, wherein the usable transverse size dimension of the SPECT device can now be fully used (i.e. the target organ size has now only to be equal at most to the detector transverse size, because the target organ has no longer to be kept within the collimator acceptance angle during the acquisition) the acquired set of planar images is complete (i.e. sufficient to reconstruct the activity distribution) and that considerable improvements with regard to the sensitivity-resolution couple can be obtained. The advantages will be evident. Better reconstructed images can be obtained by using the same acquisition time and the same dose of injected radioactivity. In this manner lesions or other malignancies in the body of a patient can be detected earlier, for example, metastasation of tumours in an early stage of development. At choice, however, the acquisition time can be reduced considerably to obtain, with the same dose of injected radioactivity, images suitable for routine investigations. This results in a reduction of the costs for the clinic or hospital. Also at choice, as a third alternative the dose of injected radioactivity can be reduced in order to burden the patient to a lesser extent. Optionally these advantages can be reached in combination with each other, then, or course, to a somewhat lesser extent but nevertheless with sufficiently attractive prospects.

Preferably, to reach superior results, the images are acquired by the method of the present invention along four linear orbits which are performed in mutually transverse directions perpendicular to the patient's body.

It should be emphasized, that by the term "target organ" is meant the organ or tissue to be studied or investigated by using the method of the invention. The term "target organ" obviously encompasses a plurality of organs to be studied simultaneously and also a part of the body, like the head, the chest or the abdomen, or even the complete body of the patient.

It is further important to note, that the linear orbits must not necessarily be straight lines, but also encompass slightly curved lines. The expression "at least substantially straight lines" may be satisfactory in this connection. The variations of the linear orbits with respect to straight lines, however, must be small to meet the requirement, that the collimator focal line is made to travel throughout the target organ during the acquisition.

It has been observed, that the quality of the reconstructed images can further be improved, if during the acquisition the fan-beam collimator remains parallel to its initial position along each orbit. This can easily be reached by shifting the collimator during the acquisition accurately parallel to the patient's body, or vice versa.

The method according to the present invention is not restricted to the use of one gamma detector provided with a fan-beam collimator (detector-collimator combination, detector-fixed fan-beam collimator), but encompasses the use of up to four detector-collimator combinations, in particular of two and four combinations additionally. More gamma cameras can be used in that case or, if desired, a two-headed or four-headed camera, i.e. a camera with two or four detector-collimator combinations. Of course, all collimators should be of the fan-beam type, focusing to a focal line. If a second detector-collimator combination is applied, this combination is used, simultaneously with and positioned opposite to the first one, sandwiching the patient in between.

If the use of four detector-collimator combinations is preferred, two couples of mutually opposite gamma detectors provided with fan-beam collimators are used simultaneously and in mutually perpendicular position, both couples sandwiching the patient in between; the images are acquired by moving each of the detector-collimator combinations along a linear orbit.

It has been observed, that by using a plurality of detector-collimator combinations, in particular two or four, according to the present invention, simultaneously following the various linear orbits, the sensitivity of the SPECT device can further be improved, resulting in still better reconstructed images.

Due to the fact that in the method of the invention the collimator focal line is made to travel throughout the target organ, so remains within the patient's body during acquisition, a fan-beam collimator or a plurality of fan-beam collimators can be used with a considerably reduced focal length, more in particular a focal length of between approx. 12 and approx. 30 cm, preferably of approx. 25 cm. As a result, the patient to be examined and also the target organ or organs can now easily be positioned within the collimator focal line where both the sensitivity and the resolution are optimal. In this pre-eminently suitable method of the invention, wherein a considerably reduced collimator focal length is used, the sensitivity can in principle be improved with a factor of approximately 10 compared with the best actual system, if a same spatial resolution is applied. This sensitivity even further increases when the size of the studied organ decreases. In addition, the reduction of the usable transverse slice size, needed to avoid image truncation, as observed in the usual SPECT technique using fan-beam collimators, is no longer present.

To improve their results, gamma cameras for SPECT imaging are often adapted to the special organs to be studied (organ-dedicated), for example, head-dedicated equipment for specific study of the head (by using an annular camera), etc. If in the method of the invention head-dedicated cameras are preferred, such cameras have only to be be equipped with fan-beam collimators with a focal length of approx. 12 cm. The method of the present invention, however, gives so much better reconstructed images, that this method is well applicable for the whole body of a patient as well as for only a part of the body, e.g. the head, without adverse effects on the quality of these images. Therefore, the method of the invention can be considered as universally applicable or allround, in that fan-beam collimators with a focal length of approximately 25 cm can be used generally, i.e. both for the whole body and for organ-dedicated SPECT imaging.

In a favourable embodiment, the method of the present invention is performed by using at least one fan-beam collimator as disclosed in U.S. Pat. No. 5,198,680 (Kurakake et al.) Such a fan-beam collimator comprises first septa members arranged in a fan-shape pattern in which all the first septa members are oriented towards a common focal line; and second septa members arranged to be parallel to each other, which second septa members are perpendicularly crossing with the first septa members in a lattice shape such that holes with a longitudinal cross section are defined between each adjacent first septa members and each adjacent second septa members.

It has further been found, that the distribution A(x,y,z) of the radioactivity in the patient's body can be computed using the following new reconstruction algorithm (this is in fact the mathematical proof that the acquired set of planar images is complete, i.e. sufficient to reconstruct the distribution activity):

$$A(x, y, z) = \frac{1}{(2\pi)^2 f} \int_{-f}^{f} dr \left( \tilde{P}_{left}\left(\frac{r}{f}x + y, r, z\right) + \tilde{P}_{under}\left(\frac{r}{f}y + x, r, z\right) + \tilde{P}_{right}\left(\frac{r}{f}x + y, r, z\right) + \tilde{P}_{over}\left(\frac{r}{f}y + x, r, z\right) \right) \quad (I)$$

$$\tilde{P}_\alpha(W, r, z) = \frac{1}{2\pi} \int_{-\infty}^{+\infty} dk e^{ikW} |k| e^{\frac{-ikU}{\alpha} \frac{r}{f}} \int_{-\infty}^{+\infty} dV e^{-ikV} P_\alpha(V, r, z)$$

wherein:
  x, y and z are the orthogonal coordinates along the horizontal transverse direction, the vertical transverse direction and the longitudinal direction, respectively;
  $P_\alpha(V,r,z)$ are the planar images pixels values, where r is the coordinate along the transverse direction of the detector and V is the detector position along the linear orbit a;
  f is the fan-beam collimator focal length; and $U_\alpha$ is the shift length of the fan-beam collimator focal line in the linear orbit a versus the origin of the axis coordinates (x=0, y=0), the said origin being located for x and y respectively at the middle of the two collimator positions in orbits left and right (under and over the radiation source, respectively).

The possibility of using a different shift length $U_\alpha$ for each linear orbit a allows to choose a special patient body region of interest, through which the collimator focal line travels during the said linear orbit a acquisition. This region can be the same for the four linear orbits in order to have the optimal sensitivity-resolution couple in this region. Alternatively, the collimator focal line can travel through a different region of interest in each linear orbit to share a high sensitivity-resolution couple among a more extended region. Furthermore, each linear orbit can be repeated with various shift lengths $U_\alpha$, reconstructed by using the algorithm disclosed hereinbefore, and then summarised to further extend the region which shares the maximum sensitivity-resolution couple.

The limit [−f,f] in the integration dr shows that the transverse size of the detector must be greater than two times the collimator focal length, according to the above algorithm. It is also important to point out that $P_\alpha(V,r,z)$ vanishes when the target organ does no longer intersept the collimator acceptance angle, and thus the integration dV, and as a result also the acquisition orbit range can be reduced, allowing an increasing acquisition time per planar image, i.e. an increasing sensitivity, for a same total acquisition time.

The above algorithm is the exact reconstruction of the acquired images under the assumption that the collimator resolution, the gamma attenuation and the gamma scatter can be neglected. If these effects should be taken in account, certain well-known iterative algorithms, like EM-ML (see hereinbefore) can additionally be used for reconstruction purposes.

In case of radioactive sources inside a homogeneous attenuation medium, the so-called Bellini method (IEEE Trans Signal Proc. 1979; 27(3): 213–218) is applicable, and leads to a projection free of attenuation $P^o(\alpha)$, using the following substitution in the fourier space of the above formula I:

$$P_\alpha^o(k, r, z) = P_\alpha\left(k, \frac{r - i\frac{\mu}{k^2}\sqrt{r^2 + f^2\left(1 + \frac{\mu^2}{k^2}\right)}}{1 + \frac{\mu^2}{k^2}}, z\right) \quad (II)$$

wherein $\mu$ is the attenuation coefficient.

The invention also relates to an equipment for performing the above method of SPECT imaging according to the invention, comprising at least one gamma camera with at least one detector-fixed fan-beam collimator, and a bed for a patient to be examined in such a relative position, that the bed is surrounded by four collimator positions, essentially situated at the angular points of a square (which are only for simplicity reasons chosen to be situated over the bed (a), under the bed (b), and on both sides (c) and (d) of the bed), which positions can be occupied by said at least one collimator focusing to a focal line parallel to the bed length. The usual equipment for imaging a patient by SPECT comprises a gamma camera with one or two (two-headed) detector-fixed collimators, which follow a revolution orbit around the patient's body. The patient to be examined is fixedly positioned on a bed. During the revolution the collimator continuously points to (faces) the body of the patient and occupies successively all collimator positions of the revolution orbit, so including the above-defined four collimator positions. If a fan-beam collimator is used in this traditional revolution orbit technique, said collimator focuses in each of these positions to a focal line parallel to the axis of rotation of the gamma camera on the other side of the patient and consequently parallel to the patient's body (see hereinbefore).

According to the present invention, the equipment for performing the above method of imaging by SPECT is characterized in that:

the bed is positionable at such a distance from the collimator positions, that in each position the collimator focal line is inside the patient's body on the bed; and the bed is adapted to allow movements vis-à-vis said at least one collimator in two perpendicular directions, both transverse to the bed length, viz. a sideward movement at position a or b of said at least one collimeter and an up and downward movement at position c or d thereof; or, alternatively, said at least one collimator is adapted to allow movements vis-à-vis the bed in perpendicular directions, all transverse to the bed length, viz. substantially parallel to the bed surface in the positions a and b, and substantially perpendicular to the bed surface in the positions c and d.

By positioning the bed at such a distance from the fan-beam collimator positions (this positioning can be adjusted by a computer, preferably by the acquisition computer), that in each of these positions the collimator focal line is inside the patient's body on the bed, the collimator focal line travels through the patient's body or the target organ therein during the acquisition by the gamma camera along linear orbits. By adapting the bed or the fan-beam collimator in such manner that it allows relative perpendicularly directed movements, as described above, images can be acquired by the gamma camera along four linear orbits performed in mutually transverse directions perpendicular to the patient's body.

The range of the relative movements of the bed vis-à-vis the collimator or collimators should preferably be at least equal to two times the transverse size of the detector or collimator, and should preferably amount to approximately 100 cm. As is already explained hereinbefore, the fan-beam collimator(s) forming part of the equipment of the invention has (have) advantageously a focal length of between approx. 12 and approx. 30 cm. If allround, i.e. not dedicated to the imaging of certain target organs or parts of the body like the head, the focal length is preferably approx. 25 cm.

It should be emphasized that by the expression "at least one" should be understood: one up to four; more in particular: one, two or four.

So the equipment according to the present invention may conveniently comprise one gamma detector provided with a fan-beam collimator. Such a detector-collimator combination is equipped in such manner that it can be moved from the above-defined position a to positions c, b and d, successively, and vice versa.

It may be of advantage, however, to include a second gamma detector provided with a fan-beam collimator into the equipment of the present invention. In that case the two detector-collimator combinations are positioned opposite to each other, sandwiching bed plus patient in between both equipped in such manner that they can be moved from position a to position c, and from position b to position d, respectively, and vice versa.

In case one or two detector-collimator combinations are present in the equipment of the invention, the equipment is preferably so adapted that the bed is movable vis-à-vis the collimator by means of a system of motive members, preferably a combination of a horizontally shifting mobile member at the foot of the bed and a jack for moving the bed into a vertical direction. This system of motive members is explained in more detail hereinafter.

In an equally advantageous embodiment the equipment of the present invention comprises four gamma detectors with fan-beam collimators, which detector-collimator combinations are so positioned that they occupy positions a, b, c and d, respectively, thereby sandwiching bed plus patient in between.

In this embodiment the four detector-collimator combinations are preferably movable vis-à-vis the bed by means of a motive system, preferably a rigid frame of four mutually perpendicular rails, positioned transversally to the bed length, along which the detector-collimator combinations can slide. This motive system is also explained in the Examples.

It is another merit of the present invention that the relative movements of the bed vis-à-vis the detector-collimator combination(s) are computer controlled (cybernation) by the gamma camera. This advanced system of computer-driven detector-collimator combination(s) relative to the patient's bed, in which the above-defined new algorithm is conveniently used, enables the user of the system, i.e. the personnel of the clinic or hospital, to investigate the patient full-automatically by the improved SPECT imaging technique of the invention.

The invention is described hereinafter with reference to joint Figures, and to the detailed description of the drawings and of model experiments.

BRIEF DESCRIPTION OF THE DRAWINGS

The invention will now be described in greater detail with reference to the accompanying drawings, wherein:

FIGS. 1 and 2 are schematic representations of the equipment according to the present invention in a suitable embodiment; FIG. 1 viewed in the longitudinal direction of the bed and FIG. 2 viewed in a direction transverse to the bed;

DETAILED DESCRIPTION OF THE DRAWINGS

Figure 1:
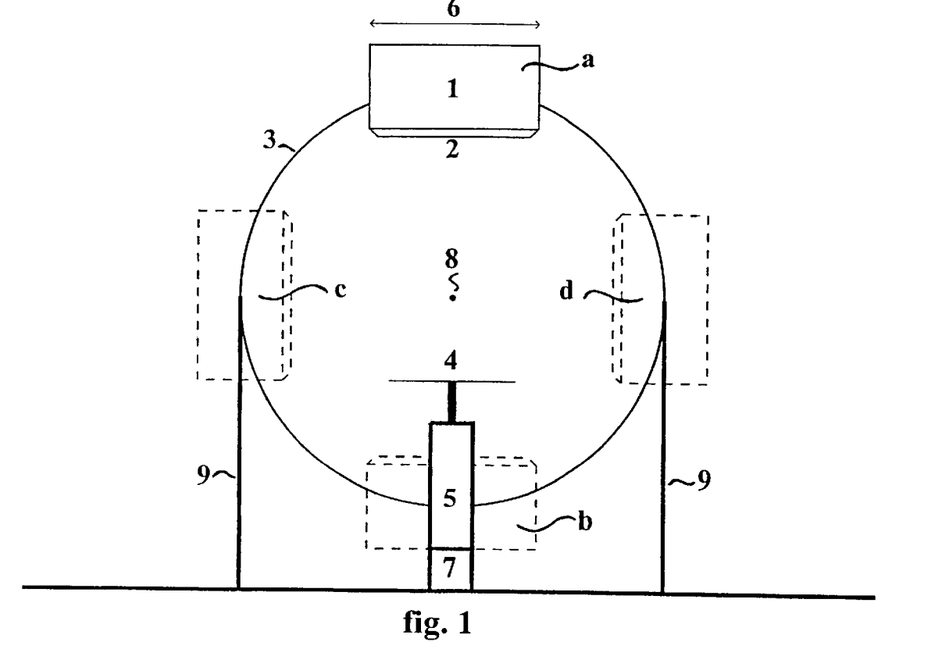
Figure 2:
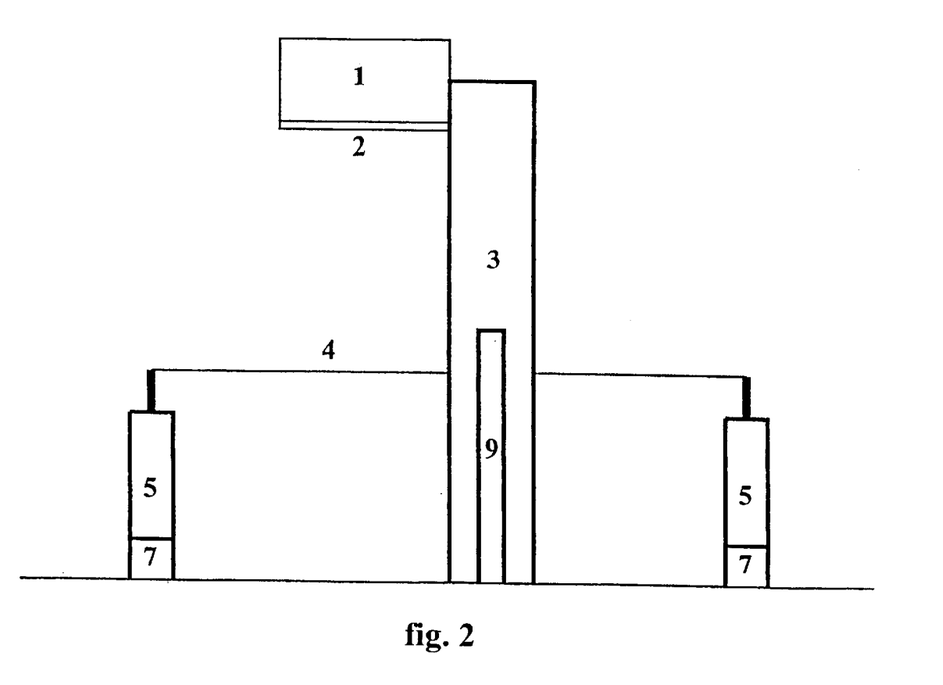

FIGS. 1 and 2 show a gamma detector 1 equipped with a fan-beam collimator 2 and movably attached to a circular rail 3 held by two pylons 9. The detector 1 can move along the rail, the collimator 2 always pointing to the rotation axis 8. Using a magnetic brake, the detector 1 can be positioned over, under, left and right the bed 4: positions a, b, c and d, respectively (the collimator centres are situated at the angular points of a sqare). A motor attached to the detector 1 and drawing an endless screw acting on a circular rack attached along the rail 3 can be used to move the detector-collimator combination from one position into another. The bed 4 can vertically move thanks to the jacks 5, which can be constituted by a motorized endless screw acting on a rack. A crenelated plate drawing by the endless screw and inserted in an optical switch can be used to adjust the vertical position of the bed 4. This bed can also move along the left-right direction of FIG. 1 (horizontal transverse direction) thanks to the mobile element 7 which can be a trolley rolling along a rail on the floor. Again a motorized endless screw acting on a rack and drawing a crenelated plate inserted in an optical switch can be used to move and adjust the transverse horizontal bed 4 position. The vertical and horizontal positioning range of the bed 4 vis-à-vis the rotation axis 8 is at least equal to two times the transverse size 6 of the detector 1. The collimator 2 focal line is parallel to the bed length and goes essentially throughout the rotation axis 8. The transverse size 6 of the detector 1 is at least equal to two times the collimator focal length. The planar images are digitally acquired along four linear orbits: the bed 4 is moved into the various successive vertical positions, when the detector 1 is unmoved left or right the bed 4 (in positions c or d, respectively); the bed is moved into the various successive transverse horizontal positions, when the detector 1 is unmoved over or under the bed 4 (in positions a or b, respectively). During acquisition, the digital planar images and the vertical and horizontal digital bed 4 positions are sent to the treatment computer. The distribution of the radioactivity over the patient's body $A(x,y,z)$, wherein x,y and z are the orthogonal coordinates along the horizontal transverse direction, the vertical direction and the longitudinal direction, respectively, can be computed using the new reconstruction algorithm as disclosed hereinbefore.

A second detector—fan-beam collimator combination may be present in position b of the above equipment, movable along the rail 3 from position b to position d and vice versa, whereas the first combination is then movable from position a to position c and vice versa.

Figure 3:
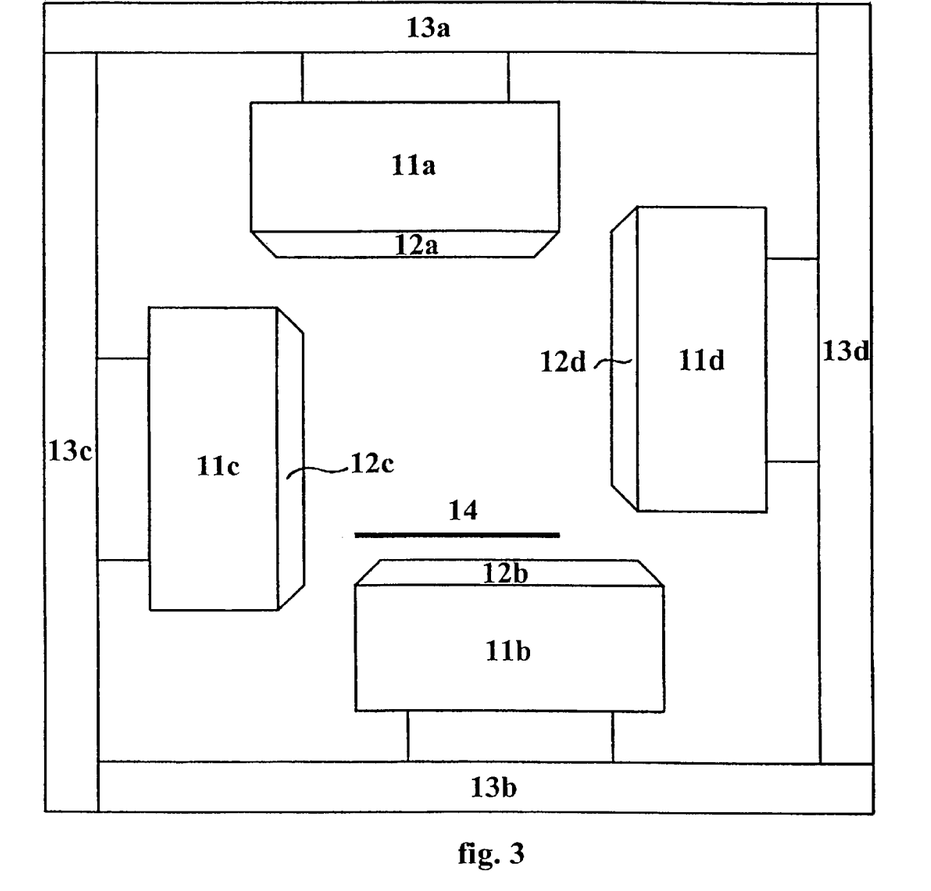
FIG. 3 is also a schematic representation of the equipment of the present invention, now in another suitable embodiment, viewed in the longitudinal direction of the bed, as in FIG. 1.

The embodiment shown in FIG. 3 comprises four gamma detectors 11a, 11b, 11c and 11d, provided with fan-beam collimators 12a, 12b, 12c and 12d, situated over, under, left and right the bed 14 (positions a, b, c and d, respectively). Each detector can be moved along a rail (13a, 13b, 13c and 13d), perpendicular to the bed 14 length; the rails are attached to each other to constitute a rigid frame.

During the acquisition the detector-collimator combinations move along their rails, the bed being unmoved.

Description of Model Experiments

To acquire real acquisition data, model experiments have been carried out. In such experiments the following requirements as to the equipment should be met:

(a) camera plus suitable fan-beam collimator;

(b) suitable radiation source; and (c) camera plus collimator should be movable vis-à-vis the radiation source or vice versa.

Ad (a). A suitable fan-beam collimator, meeting the requirements of the present invention, in particular a collimator having a suitable focal length, is not commercially available. Therefore one has resorted to the use of a home-made collimator. This fan-beam collimator, having a hole length of 25 mm and a hole diameter of 1.5 mm, is deficient in various respects, viz.

(i) the shaped holes are not correctly dimensioned, giving a focal band instead of a focal line at the desired focal distance;

(ii) the number of holes is insufficient, leading to an insufficient measured radioactivity; and (iii) the focal length increases as the holes are situated at a greater distance from the centre of the collimator.

These defects will have an unfavourable influence on the results obtained, in particular on the spatial resolution and/or the sensitivity.

Ad (b). As the radiation source is used a so-called Jaszczak's de luxe phantom, well-known in the art of performing radioactive experiments.

Ad (c). The radiation source is movable relative to the collimator in such manner that it enables the acquisition of images along linear orbits performed in two directions x and y (horizontal and vertical), perpendicular to the SPECT camera rotation axis z.

Figure 4A:
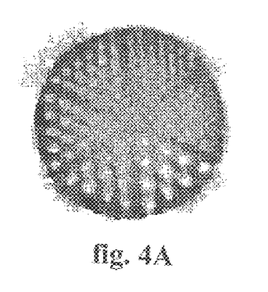
FIGS. 4 and 5 show SPECT spatial revolution images, obtained by performing model experiments.

In the above arrangement, the method of the present invention is performed with the radiation source centre situated at a distance of approx. 20 cm from the fan-beam collimator. After an acquisition time of 90 minutes, the SPECT spatial resolution of FIG. 4A is obtained; the total number of counts is measured and amounts to 52 Mc.

Figure 4B:
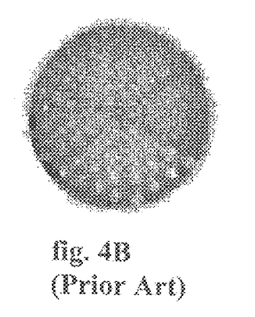
Figure 4C:
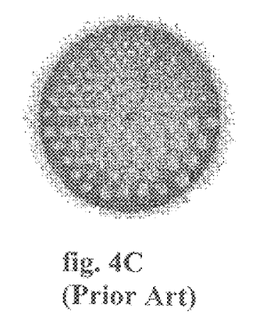

In comparison, two commercially available parallel-hole collimators, viz. a low energy high resolution collimator (LEHR; hole length 40 mm, hole diameter 1.8 mm) and a low energy ultra high resolution collimator (LEUHR; hole length 45 mm, hole diameter 1.8 mm) are used in the prior art SPECT method, viz. with a gamma camera following a revolution orbit around the radiation source. After an acquisition time of 90 minutes, the SPECT spatial resolutions are shown in FIGS. 4B and 4C, respectively; the measured numbers of counts are 27 Mc and 22 Mc, respectively.

From the Figures it can be concluded, that the spatial resolution obtained according to the method of the invention is considerably better than by using the LEHR collimator and also still better than with the LEUHR one. In comparison with the LEUHR collimator, the sensitivity improvement obtained is 2.36 (55/22) with simultaneously a significant improvement of the spatial resolution (approx. 1.5). Such an improvement is beyond expectation in view of the deficiency of the home-made fan-beam collimator used, as explained above.

Figure 5A:
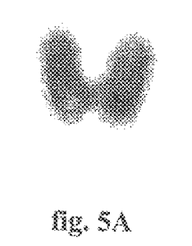
Figure 5B:
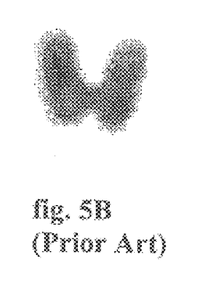

In the same manner acquisition data are obtained by using a thyroid phantom as the radiation source. By using in the method of the present invention again the above home-made fan-beam collimator, the SPECT spatial resolution of FIG. 5A is obtained after an acquisition time of 90 minutes. By using in the prior art SPECT method the above-described parallel-hole LEHR collimator, an approximately equal spatial resolution is obtained after the same acquisition time: FIG. 5B. By using the commercial parallel-hole collimator, a total number of counts of 3.1 Mc is measured, whereas, by using a collimator according to the method of the invention, on the other hand, a total number of counts of 16.1 Mc is monitored, i.e. a sensitivity improvement of approximately 5.

What is claimed is:

1. A method of imaging a target organ in a patient by SPECT, by using a gamma camera having a detector/collimator combination including a gamma detector provided with a fan-beam collimator, comprising:
   focusing the collimator to a focal line parallel to the patient's body length;
   acquiring planar images by relative movement between the gamma camera and the patient's body along at least on linear path in a direction perpendicular to the patient's body length so that the collimator focal line traverses said target organ; and
   computer reconstructing the distribution of the radioactivity inside the patient's body from the acquired planar images by using reconstruction algorithms.

2. The method of claim 1, wherein the images are acquired along four, mutually orthogonal, linear paths in directions perpendicular to the patient's body length.

3. The method of claim 1, wherein the collimator remains parallel to its initial position along each linear path.

4. The method of claim 1, wherein two detector/collimator combinations are used simultaneously and in positions on opposite sides of the patient's body.

5. The method of claim 1, wherein four detector/collimator combinations are used simultaneously and each two of the four detector/collimator combinations are positioned on opposite sides of the patient's body, and wherein the images are acquired by moving each of the detector/collimator combinations along a linear path.

6. The method of claim 1, wherein at least one gamma detector is used with at least one fan-beam collimator having a focal length of between about 12 and 30 cm.

7. The method of claim 6, wherein the focal length of the at least one fan-beam collimator is about 25 cm.

8. The method of claim 6, wherein the fan-beam collimator comprises first septa members arranged in a fan-shape pattern in which all the first septa members are oriented towards a common focal line, and second septa members arranged to be parallel to each other, the second septa members perpendicularly crossing with the first septa members in a lattice shape such that holes with a longitudinal cross section are defined between each adjacent first septa member and each adjacent second septa member.

9. A method of any one of claims 2–8, wherein the following reconstruction algorithm, is used:

$$A(x, y, z) = \frac{1}{(2\pi)^2 f}$$

$$\int_{-f}^{f} dr \left( \tilde{P}_{left}\left(\frac{r}{f}x + y, r, z\right) + \tilde{P}_{under}\left(\frac{r}{f}y + x, r, z\right) + \tilde{P}_{right}\left(\frac{r}{f}x + y, r, z\right) + \tilde{P}_{over}\left(\frac{r}{f}y + x, r, z\right) \right)$$

$$\tilde{P}_\alpha(W, r, z) = \frac{1}{2\pi} \int_{-\infty}^{+\infty} dk e^{ikW} |k| e^{-ikU_\alpha \frac{r}{f}} \int_{-\infty}^{+\infty} dV e^{-ikV} P_\alpha(V, r, z)$$

where x, y and z are the orthogonal coordinates along the horizontal transverse direction, the vertical transverse direction and the longitudinal direction, respectively;

$P_\alpha(V, r, z)$ are the planar images pixels values, where r is the coordinate along the transverse direction of the detector and V is the detector position along the linear orbit a;

f is the fan-beam collimator focal length; and $U_\alpha$ is the shift length of the fan-beam collimator focal line in the linear orbit a versus the origin of the axis coordinates (x=0, y=0).

10. Apparatus for imaging a target organ in a patient by SPECT, comprising:
   at least one gamma camera having at least one detector/collimator combination including a gamma detector and a fan-beam collimator fixed to the gamma detector,
   a bed for a patient to be examined and having a bed length;
   means for defining collimator positions located respectively at the corners of a rectangle normal to the bed length to surround the bed, and including a first position over the bed, a second position under the bed, a third position on one side of the bed, and a fourth position on the side of the bed opposite the third position, the at least one collimator being positionable at all of the first, second, third, and fourth positions, and focusing to a focal line parallel to the bed length;
   means for positioning the bed at such a distance from the collimator positions, that the collimator focal line is inside the patient's body on the bed in each of the collimator positions; and
   means for moving the bed in two perpendicular directions, both transverse to the bed length, to effect a horizontal movement at the first and second positions of said at least one collimator and a vertical movement at the third and fourth positions.

11. The apparatus of claim 10, wherein the means for positioning the bed comprises a system of motive members including a horizontally shifting mobile member at the foot of the bed and a jack for moving the bed in a vertical direction.

12. Apparatus for imaging a target organ in a patient by SPECT, comprising:

at least one gamma camera having at least one detector/collimator combination including a gamma detector and a fan-beam collimator fixed to the gamma detector, a bed for a patient to be examined and having a bed surface and a bed length;

collimator positions located respectively at the corners of a rectangle normal to the bed length to surround the bed, and including a first position over the bed, a second position under the bed, a third position on one side of the bed, and a fourth position on the side of the bed opposite the third position; the at least one collimator being positionable at all of the first, second, third, and fourth positions, and focusing to a focal line parallel to the bed length;

means for positioning the bed at such a distance from the collimator positions, that the collimator focal line is inside the patient's body on the bed in each of the collimator positions; and means for moving the at least one collimator in two perpendicular directions, both transverse to the bed length, to effect movement parallel to the bed surface at the first or second positions of said at least one collimator and movement perpendicular to the bed surface at the third and fourth positions.

13. The apparatus of any one of claims 10 or 12, wherein the range of the relative movement between the bed and the at least one collimator is at least equal to two times the transverse size of said detector or collimator.

14. The apparatus of claim 13, wherein the range of the relative movement between the bed and the at least one collimator is approximately 100 cm.

15. The apparatus of any one of claims 10 or 12, wherein said at least one collimator has a focal length of between about 12 and 30 cm.

16. The apparatus of claim 15, wherein said at least one collimator has a focal length of about 25 cm.

17. The apparatus of any one of claims 10 or 12, comprising a single gamma detector/collimator combination movable from the first position to the second, third and fourth positions, successively.

18. The apparatus of any one of claims 10 or 12 comprising two gamma detector/collimator combinations, positioned on opposite sides of the bed, and moveable respectively from the first position to the third position, and from the second position to the fourth position.

19. The apparatus of any one of claims 10 or 12, comprising four gamma detector/collimator combinations positioned at the first, second, third and fourth positions, respectively.

20. The apparatus of claim 19, wherein the detector/collimator combinations are movable relative to the bed by means of a motive system including a rigid frame of four mutually perpendicular rails, positioned transversally to the bed length, along which the detector/collimator combinations can slide.

21. The apparatus of any one of claims 10 or 12, wherein the relative movement between the bed and the detector/collimator combinations are computer controlled by the gamma camera.

* * * * *

UNITED STATES PATENT AND TRADEMARK OFFICE
CERTIFICATE OF CORRECTION

PATENT NO. : 6,469,306 B1
DATED : October 22, 2002
INVENTOR(S) : Adrianus A. Van Dulmen and Stéphan Walrand It is certified that error appears in the above-identified patent and that said Letters Patent is hereby corrected as shown below:

<u>Title page,</u>
Item [76], delete in its entirety and substitute therefore:

-- [75] Inventors: Adrianus A. Van Dulmen, Shoutsakker 4, NL-1871, CZ Schoorl (NL); Stéphen Walrand, 31, rue de Baileux, B-5630 Silenrieux (BE)

[73] Assignee: Andrianus A. Van Dulmen, CZ Schoorl, The Netherlands --.

<u>Column 9,</u>
Line 54, "on" should read -- one --.

Signed and Sealed this

Eleventh Day of February, 2003

JAMES E. ROGAN
*Director of the United States Patent and Trademark Office*